(12) United States Patent
Pigamo et al.

(10) Patent No.: US 8,779,218 B2
(45) Date of Patent: Jul. 15, 2014

(54) PROCESS FOR THE MANUFACTURE OF 2-CHLORO-3,3,3-TRIFLUOROPROPENE (HFCO 1233XF) BY LIQUID PHASE FLUORINATION OF PENTACHLOROPROPANE

(75) Inventors: Anne Pigamo, Chaponost (FR); Laurent Wendlinger, Soucieu en Jarrest (FR); Philippe Bonnet, Lyons (FR)

(73) Assignee: Arkema France, Colombes (FR)

( * ) Notice: Subject to any disclaimer, the term of this patent is extended or adjusted under 35 U.S.C. 154(b) by 71 days.

(21) Appl. No.: 13/642,589

(22) PCT Filed: Mar. 21, 2011

(86) PCT No.: PCT/IB2011/000777
§ 371 (c)(1),
(2), (4) Date: Oct. 22, 2012

(87) PCT Pub. No.: WO2011/135416
PCT Pub. Date: Nov. 3, 2011

(65) Prior Publication Data
US 2013/0041190 A1 Feb. 14, 2013

Related U.S. Application Data

(60) Provisional application No. 61/327,817, filed on Apr. 26, 2010.

(30) Foreign Application Priority Data

Apr. 26, 2010 (WO) .................. PCT/IB2010/001284
Nov. 15, 2010 (WO) .................. PCT/IB2010/003157

(51) Int. Cl.
*C07C 17/23* (2006.01)
*C07C 17/25* (2006.01)

(52) U.S. Cl.
USPC ........................... 570/156; 570/165; 570/228

(58) Field of Classification Search
USPC .......................................... 570/156
See application file for complete search history.

(56) References Cited

U.S. PATENT DOCUMENTS

| | | | | |
|---|---|---|---|---|
| 4,091,043 A | * | 5/1978 | Ohsaka et al. | 570/170 |
| 4,885,416 A | * | 12/1989 | Mader | 570/170 |
| 5,336,816 A | * | 8/1994 | Achord et al. | 570/188 |
| 5,714,652 A | | 2/1998 | Grunchard et al. | |
| 6,881,698 B2 | | 4/2005 | Bonnet et al. | |
| 2004/0186323 A1 | * | 9/2004 | Banister et al. | 568/451 |
| 2009/0240090 A1 | | 9/2009 | Merkel et al. | |
| 2010/0036179 A1 | * | 2/2010 | Merkel et al. | 570/156 |
| 2010/0185029 A1 | | 7/2010 | Elsheikh et al. | |
| 2010/0191025 A1 | * | 7/2010 | Perdrieux | 570/155 |

FOREIGN PATENT DOCUMENTS

| | | |
|---|---|---|
| WO | WO 90/08754 | 8/1990 |
| WO | WO 2007/079431 A2 | 7/2007 |
| WO | WO 2008127940 A1 * | 10/2008 |
| WO | WO 2009015317 A1 * | 1/2009 |

* cited by examiner

*Primary Examiner* — Jafar Parsa
*Assistant Examiner* — Medhanit Bahta
(74) *Attorney, Agent, or Firm* — Brinks Gilson & Lione

(57) ABSTRACT

Process of catalytic fluorination in liquid phase of product 1,1,1,2,3-pentachloropropane or/and 1,1,2,2,3-pentachloropropane into product 2-chloro-3,3,3-trifluoropropene in presence of a catalyst.

20 Claims, 2 Drawing Sheets

PROCESS FOR THE MANUFACTURE OF 2-CHLORO-3,3,3-TRIFLUOROPROPENE (HFCO 1233XF) BY LIQUID PHASE FLUORINATION OF PENTACHLOROPROPANE

This application claims priority to International Application for Patent Serial Number PCT/IB2011/000777 filed Mar. 21, 2011, which claims priority to International Application for Patent Serial Number PCT/IB2010/003,157 filed Nov. 15, 2010 and International Application for Patent Serial Number PCT/IB2010/001284 filed Apr. 26, 2010 and U.S. Provisional Application for Patent Ser. No. 61/327,817 filed Apr. 26, 2010.

FIELD OF THE INVENTION

The aim of the invention is the catalytic fluorination in liquid phase of product 1,1,1,2,3-pentachloropropane (HCC 240 db) and/or 1,1,2,2,3-pentachloropropane (HCC 240aa) into product 2-chloro-3,3,3-trifluoropropene (HCFO 1233xf).

TECHNICAL BACKGROUND

The protocol of Montreal for the protection of the ozone layer led to the end of the use of chlorofluorocarbons (CFCs). Less aggressive compounds for the ozone layer, such as the hydrofluorocarbons (HFCs) e.g. HFC-134a replaced chlorofluorocarbons. These latter compounds were indeed shown to provide greenhouse gases. There exists a need for the development of technologies, which present a low ODP (ozone depletion potential) and a low GWP (global warming potential). Although the hydrofluorocarbons (HFCs), which are compounds which do not affect the ozone layer, were identified as interesting candidates, they exhibit a relatively high GWP value. There still exists the need to find compounds which exhibit a low GWP value. Hydrofluoroolefins (HFO) were identified as being possible alternatives with very low ODP and GWP values.

Several processes for production of HFOs compounds, in particular of propenes, were developed. The two compounds 1233xf (2-chloro-3,3,3-trifluoropropene) and 1234yf (2,3,3,3-tetrafluoropropene) are particularly desired.

WO2008/149011 describes fluorination in liquid phase in the presence of an ionic liquid of a propene. It is indicated generally that 1233xf and/or 1234yf (2,3,3,3-tetrafluoropropene) can be obtained by conversion of 1230xa.

WO2009/003157 discloses in its example 3 an alleged process for the conversion of 240db. In this example, the reactor is first charged with HF and the organic, and then the reaction is said to proceed towards product 245eb (1,1,1,2,3-pentafluoropropane).

WO2007/079431 in the example 3, discloses the reaction of product 240aa in a NaOH solution to provide the corresponding unsaturated compound, which necessitates a further, distinct, fluorination step for its conversion into 1233xf.

WO90/08754 discloses in example 4-1 the fluorination of 240aa. In this example, the reactor is charged with the organic compound and with HF, and the catalyst is antimony pentachloride. The reaction products comprise products of the 241(tetrachlorofluoropropane), 242(trichlorodifluoropropane), 243(dichlorotrifluoropropane) and 244(chlorotetrafluoropropane) series.

Thus, there is still a need for processes for the production of compound 1233xf.

SUMMARY OF THE INVENTION

The invention provides a process of catalytic fluorination in liquid phase of product 1,1,1,2,3-pentachloropropane or/and 1,1,2,2,3-pentachloropropane into product 2-chloro-3,3,3-trifluoropropene in presence of a catalyst.

Embodiments are the following:

the process is carried out in an organic medium, optionally in a solvent, which when used can be present in a quantity for a dilution ratio from at least 20%, preferably between 20% and 80%, advantageously between 40% and 60%. The solvent can be selected from 1,2-dichloroethane, 1,2,3-trichloropropane, 1-chloro-1-fluoroethane, 1,1-difluoroethane, 1,1-dichloroethane and 1,3-dichloro-1-fluorobutane, tetrachlorofluoropropane isomers, trichlorodifluoropropane isomers and dichlorotrifluoropropane isomers, 1,1,1,3,3-pentafluorobutane and 1,1,2-trichloro-2,2-difluoroethane, nitrated solvents including nitromethane and nitrobenzene, sulfones including tetramethylene sulfone and dimethyl sulfone, 1,1,2-trichloro-2-fluoroethane or perchloroethylene, or mixtures thereof, preferably 1,1,2-trichloro-2,2-difluoroethane.

The catalyst is preferably an ionic liquid. The molar ratio catalyst/organics can be between 2 mol % and 90 mol %, preferably between 4 mol % and 80 mol % and more preferably between 6 mol % and 75 mol %.

chlorine is added during the reaction, preferably according to a molar ratio from 0.05 to 20 mole %, preferably 0.5 to 15 mole % of chlorine per mole of starting compound.

a gas is injected, preferably anhydrous HCl. the flow of gas, compared to the flow of the starting product lies between 0.5:1 and 5:1, advantageously, between 1:1 and 3:1.

the product of the reaction is withdrawn in the gaseous state.

the 1,1,1,2,2-pentachloropropane contains up to 20 mol % of isomer 1,1,2,2,3-pentachloropropane.

the temperature of the reaction ranges between 30° C. and 200° C., preferably between 40° C. and 170° C., advantageously between 50° C. and 150° C.

the pressure of the reaction is higher than 2 bar, preferably between 4 and 50 bar, in particular between 5 and 25 bar.

the molar ratio of HF:starting compound lies between 0.5:1 and 50:1, preferably between 3:1 with 20:1, advantageously about 5:1.

a stabilizer is used, preferably chosen from the group consisting of p-methoxyphenol, t-amylphenol, thymol, limonene, d,l-limonene, quinones, hydroquinones, epoxides, amines and their mixtures. The amount can be 5-1000 ppm, preferably 10-500 ppm.

the process preferably comprises:
(i) contacting 1,1,1,2,3-pentachloropropane or/and 1,1,2,2,3-pentachloropropane with hydrogen fluoride in a liquid phase in an organic medium under conditions sufficient to form a reaction mixture comprising 2-chloro-3,3,3-trifluoropropene;
(ii) separating the reaction mixture into a first stream comprising HCl, and a second stream comprising HF and 2-chloro-3,3,3-trifluoropropene.

the second stream comprises between 30 mol % and 70 mol % of 1233xf, between 30 mol % and 70 mol % of HF and less than 10 mol %, preferably less than 5 mol %, of compounds of the series 242 and 243.

step (ii) can be a distillation step. The second stream can be further separated, preferably by decantation, into a HF stream containing mainly HF, and an organic stream containing 2-chloro-3,3,3-trifluoropropene. The organic stream can be further purified. The process can further comprise a purging step for withdrawing heavies formed during step (i).

the process is carried out continuously.

DETAILED DESCRIPTION OF EMBODIMENTS

Figure 1:
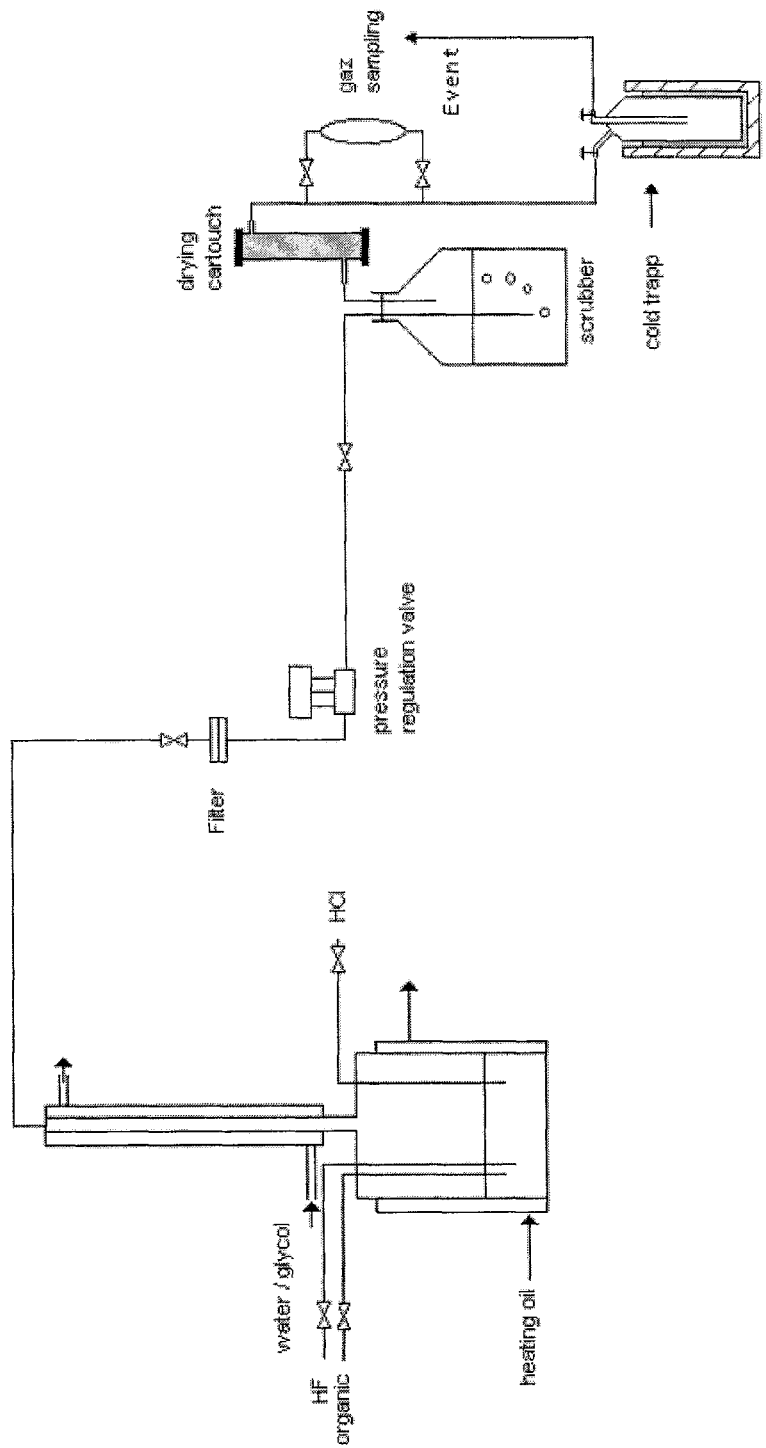
FIG. 1 is a representation of the experimental device used in the examples.

The invention is based on the surprising findings that 240db/240aa can be fluorinated in liquid phase into 1233xf, and that process conditions can be selected so as to achieve the reaction with a substantial selectivity into the desired product.

In a preferred embodiment, the liquid phase process is carried out in an organic phase. Using an organic phase rather than an HF phase favors the reaction into 1233xf. The prior art reported above disclose reaction mixtures comprising a substantial part of HF, hence an acidic phase. In an acidic phase, only saturated products are produced. The applicant has found that, surprisingly, there exist conditions that allow fluorination into 1233xf. Notably, when the reaction is carried out in an organic phase (comprised of the 240 starting material and/or solvent), then 1233xf can be formed. When HF is added to an initial medium, it will not remain in the medium since it reacts and the amount of HF (or concentration) will be very low, compared to the other products.

The term "organic phase" can thus be defined as referring to a reaction phase comprising the catalyst and the starting material and possibly a solvent if used, but substantially free of HF. Especially the process carried out in an "organic phase" refers to the process in which the initial load does not comprise any HF, in contrast with the prior art.

Because of particular operating conditions, gaseous 1233xf can be removed from the reactor under gaseous phase, keeping polymerization reactions at a low level.

The liquid phase fluorination of 240db/240aa into 1233xf is carried out in the presence of a catalyst.

The reaction can be implemented in a liquid solvent medium, the reaction zone being either loaded at the beginning with a starting amount of organic (the starting material) and/or the necessary quantity of solvent, or fed continuously with this quantity of solvent (possibly preliminary mixed with the raw material). When carried out with solvent, it is preferred that the solvent be loaded at the beginning; injections with a view of adjusting the quantity of solvent may however be carried out if necessary.

The reaction conditions (notably pressure) are such that the reactants are liquid. According to an embodiment the reactants are liquid while the reaction product is gaseous. The fact that the reaction products are gaseous allows their recovery in a gaseous phase at the exit of the reaction zone. The intermediate product, especially the 242 compound (trichlorodifluoropropane), is preferably liquid under the reaction conditions, even though it can be stripped away in the gaseous flow.

According to the invention, this stage is in particular implemented under a pressure higher than 2 bar. Advantageously, the pressure lies between 4 and 50 bar, in particular between 5 and 25 bar.

For example, the reaction may be implemented at a temperature ranging between 30° C. and 200° C., preferably between 40° C. and 170° C., advantageously between 50° C. and 150° C.

The molar ratio HF:starting compound lies generally between 0.5:1 and 50:1, preferably between 3:1 and 20:1. Values of about 5:1 can be used with advantage. The amount of HF added will correspond to the stoichiometry of the reaction (here 3), to which one will add the amount of HF that is present in the exiting streams (HF and organics) which are usually azeotropic mixtures.

The other reaction conditions, notably flow rates, can be determined by the skilled person according to common general knowledge, depending on the temperature, pressure, catalyst, reactant ratios, and the like. One shall take care that further fluorination reactions should be avoided so that 1233xf is the main product obtained (apart intermediate products).

The solvent, if used, is an inert organic solvent under the reaction conditions. Such a solvent will be generally saturated, advantageously in C2 to C6, in order to avoid the reactions of addition. Such solvents can for example be those mentioned in patent application FR2733227. Such solvents have a boiling point (measured at atmospheric pressure), for example higher than 40° C., advantageously higher than 50° C., in particular higher than 60° C. Higher reaction temperatures will imply higher pressures, so that the boiling point of the solvent under the conditions of reaction is higher than the temperature of implementation of the reaction.

One can in particular mention as a solvent the saturated compounds of ethane, propane or butane, substituted by at least two atoms of halogen, chosen among chlorine and fluorine, or a mixture thereof. As an example one can mention 1,2-dichloroethane, 1,2,3-trichloropropane, 1-chloro-1-fluoroethane, 1,1-difluoroethane, 1,1-dichloroethane and 1,3-dichloro-1-fluorobutane, tetrachlorofluoropropane isomers, trichlorodifluoropropane isomers and dichlorotrifluoropropane isomers, 1,1,1,3,3-pentafluorobutane and 1,1,2-trichloro-2,2-difluoroethane, or a mixture thereof. Nitrated solvents like nitromethane or nitrobenzene and sulfones like tetramethylene sulfone (also known as sulfolane) or dimethyl sulfone may also be used. A preferred solvent is the 1,1,2-trichloro-2,2-difluoroethane (F122). One can also use possibly reactive solvents, in so far as the product of their reaction is a nonreactive solvent. For example, one can also use the precursor of F122, namely F121 ($CCl_2F—CHCl$, 1,1,2-trichloro-2-fluoroethane) or perchloroethylene.

The solvent can be present in a quantity for a dilution ratio from at least 20%, preferably between 20% and 80%, advantageously between 40% and 60%.

The reaction is catalyzed. The catalysts may be catalysts known by the person skilled in the art of fluorinations in liquid phase.

One can use an acid of Lewis, a catalyst containing a metal halide, in particular containing halide of antimony, tin, tantalum, titanium, metals of transition such as molybdenum, niobium, iron halides, cesium, oxides of metals of transition, halides of metals of the IVb group, halides of metals of the Vb group, a fluorinated chromium halide, a fluorinated chromium oxide or a mixture of both. One can advantageously use metal chlorides and fluorides. Examples of such catalysts include: $SbCl_5$, $SbCl_3$, $TiCl_4$, $SnCl_4$, $TaCl_5$, $NbCl_5$, $TiCl_4$, $FeCl_3$, $MoCl_6$, $CsCl$, and their corresponding fluorinated derivatives. Pentavalent metal halides are suitable.

Advantageously one will use a catalyst containing an ionic liquid. These ionic liquids are particularly interesting for fluorination by HF in liquid phase. One will be able to mention the ionic liquids described in patent applications WO2008/149011 (in particular from page 4, line 1 to page 6 line 15, included by reference) and WO01/81353 in the name of the applicant, as well as the reference "liquid-phase HF Fluorination", Multiphase Homogeneous Catalysis, Ed. Wiley-VCH, (2002), 535.

One can operate with variable ratios catalyst/organic (including solvent if used), but in general one will prefer that this molar ratio lies between 2 mol % and 90 mol %, preferably between 4 mol % and 80 mol % and more preferably between 6 mol % and 75 mol %.

The starting material can be substantially pure 240db, and/or substantially pure 240aa, or it can be a mixture of the two. In one embodiment, the starting material can be a typical 240db feed, i.e. one containing the 240aa isomer in an amount up to 20%.

A chlorine stream may be used to increase the lifetime of the catalyst, typically in a quantity from 0.05 to 20 mole %, preferably 0.5 to 15 mole % of chlorine per mole of starting compound 240db/240aa. Chlorine may be introduced pure or mixed with an inert gas such as nitrogen. The use of an ionic catalyst allows using small quantities of chlorine.

A raw material stabilizer may be used if necessary; typically in a quantity of 5-1000 ppm, preferably 10-500 ppm. This stabilizer can be for example p-methoxyphenol, t-amylphenol, thymol, limonene, d,l-limonene, quinones, hydroquinones, epoxides, amines and their mixtures.

It is also possible that the product of the reaction be stripped using a light gas allowing its drive by mechanical entrainment. Removing gaseous 1233xf from the liquid phase reactor keep polymerization reactions at a low level (since polymerizable material is in a low amount in the medium) as well as side-reactions (such as addition onto the double bond of the 1233xf). The addition of a gaseous compound can be advantageous for the reaction, which can be favored for example by the improvement of agitation (bubbling).

This gas can be inert as the nitrogen or helium or the gas can be preferably HCl. When HCl is used, the reaction performs despite the addition into the medium of HCl, which is a reaction product.

Advantageously, this added gas is anhydrous hydrochloric acid. The flow of the stripping gas is determined according to the operating conditions. For example, the flow of HCl, compared to the flow of starting product is such that the molar ratio HCl: starting product lies between 0.5:1 and 5:1, advantageously, between 1:1 and 3:1.

The fluorination process in liquid phase according to the invention can be implemented continuously or semi-continuously. According to the preferred embodiment, the process is continuous.

The reactants (starting product and HF) and other compounds used in the reaction (chlorine, anhydrous HCl) can be fed in the reactor at the same place or at different places of the reactor. A preferred embodiment is when the gaseous compounds are injected in the bottom of the reactor, in particular in order to enhance the mechanical stripping and the mixing.

If a recycling is used, one can recycle directly at the inlet of the reactor or on a separate dip pipe.

The reaction is implemented in a reactor dedicated to the reactions involving halogens. Such reactors are known by the skilled worker and can comprise coatings containing Hastelloy®, Inconel®, Monel® or fluoropolymers. The reactor can be equipped with means for heat transfer.

Figure 2:
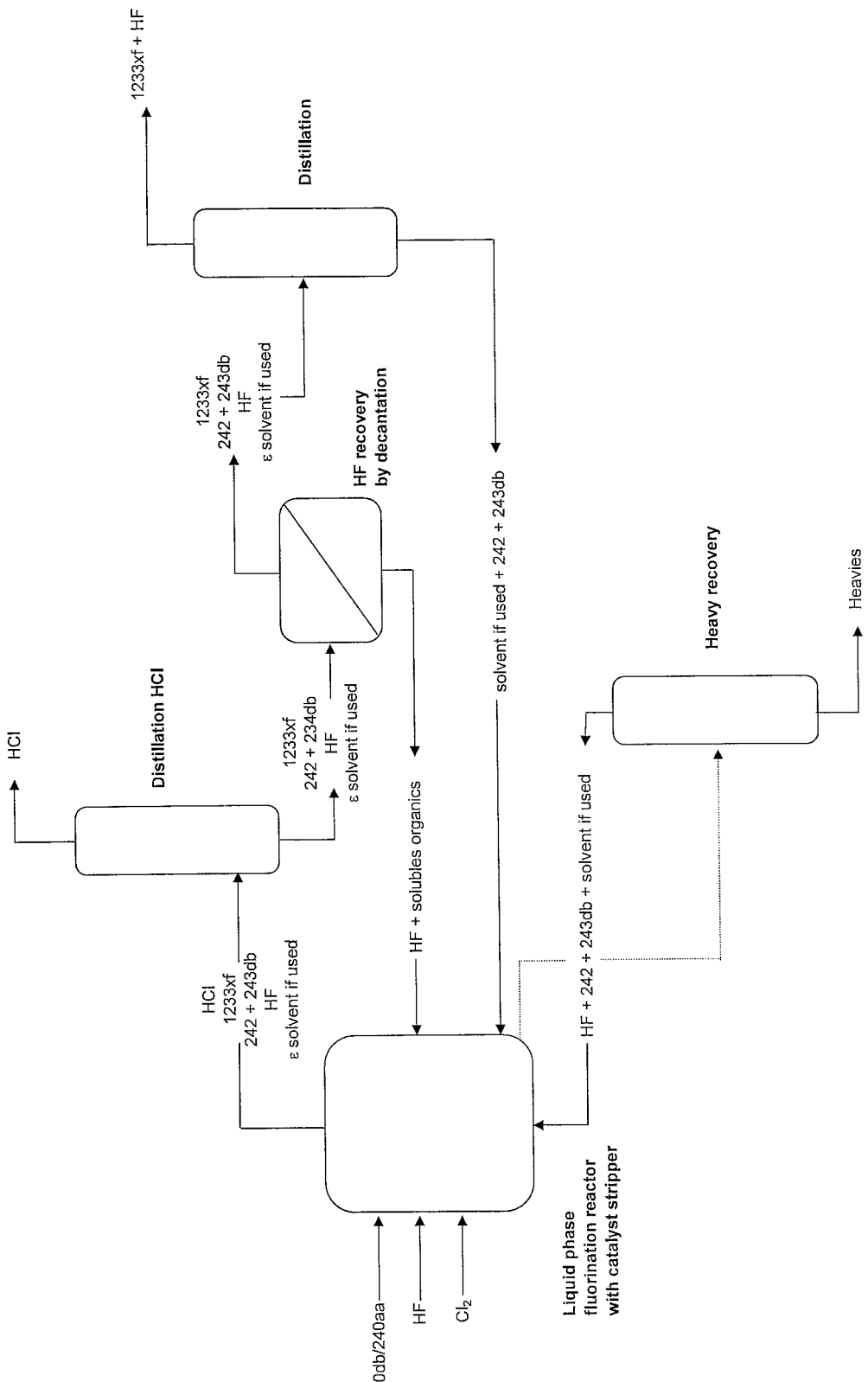
FIG. 2 is a schematic representation of a process implementing the invention.

FIG. 2 is a schematic representation of a process according to an embodiment of the invention. The reactor (equipped with a catalyst stripping column, not shown in the figure) for the liquid phase reaction is loaded with catalyst, pentachloropropane and solvent if used. Then pentachloropropane and HF are supplied continuously. A stream of anhydrous HCl could also be injected.

The stream which is withdrawn from the reaction zone is in a gaseous form and mainly comprises 1233xf, HCl, HF as well as traces of stripped solvent 122 if any and other by-products including 242 isomers, and possibly 243 (dichlorotrifluoropropane) especially 243db (1,1,1-trifluoro-2,3-dichloropropane). This stream is introduced into a distillation column of HCl. At the top of the column is withdrawn a stream of HCl; at the bottom of the column a stream containing 1233xf, 242, HF as well as traces of 122 and 243db is withdrawn. Typically, this bottom stream will comprise between 30 mol % and 70 mol % of 1233xf, between 30 mol % and 70 mol % of HF as well as minor amounts, typically less than 10 mol %, preferably less than 5 mol %, of compounds of the series 242, 243 (especially 243db). This stream is sent towards a stage of separation by decantation. This decantation leads to two streams. The first stream comprises HF and soluble organics and solvent if any. This HF-rich stream is returned to the fluorination reaction. The second stream comprises 1233xf, 242, still a quantity of HF as well as traces of 122 and 243db. This stream is sent in a distillation column to be separated there. The traces of 122 and 243db are recovered at the bottom and are returned towards the fluorination reactor. The 242 product (and generally the higher saturated fluorinated products of the 240 series) will not build up, since it is an intermediate compound. A stream containing HF and 1233xf is withdrawn at the top. This top stream can be further separated or can be sent directly towards the next step. 242 isomers and/or 243db can be recycled in the process of the invention.

At the bottom of the liquid phase reactor a stream containing the heavies is withdrawn. It is believed, without wishing to be bound, that the heavies comprise oligomers of the $C_6F_6H_2Cl_2$ type. The bottom of the fluorination reactor is purged with a flow and a frequency such that the accumulation of heavies is avoided (rate of purging being defined by both a flow and frequency of purging as the skilled person can easily determine). This stream is treated in a column of recovery of the heavies. These heavies are eliminated at the bottom of this column. At the top of the column a stream containing HF, 122 and 242 isomers and 243db is recovered; this stream is recycled towards the fluorination reactor.

EXAMPLES

The following examples illustrate the invention without limiting it.

Equipment used is described with reference to FIG. 1. It consists of a jacketed autoclave of a capacity of 1 liter, made of stainless steel 316L, which is stirred using a magnetic stirrer. It is equipped with pressure and temperature indicators. Apertures on the head of the autoclave allow the introduction of the reactants and degasification. It comprises at the top a condenser as well as a valve for regulating the pressure. The condenser is controlled in temperature using an independent thermostated bath.

The products of the reaction are extracted continuously during the reaction. They enter a scrubber which collects hydracids HF and HCl and then are cold trapped in liquid nitrogen. The increase of weight of the scrubber and of the trap makes it possible to establish a mass balance.

At the end of the period of reaction, the reaction medium is degassed in order to evacuate residual HF. For this period of degasification, the organics possibly drawn are also trapped, always after having crossed the scrubber which makes it possible to eliminate HF and HCl from the gas flow. In a last stage, the autoclave is opened and drained, a sample of the organic phase is analyzed after having hydrolyzed and extracted the catalyst with a hydrochloric acid solution.

The analysis is made then by gas phase chromatography on a sample of expanded liquid. The analysis by chromatography is carried out using a column CP Sil 8, dimensions 50 m*0.32 mm*5 μm. The programming of temperature of the furnace is the following one: 40° C. during 10 min then slope of 4° C./min until 200° C.

Considering that xi is the initial amount of moles of raw material and xf the total final amount of moles of raw material, conversion (%) is: (xi−xf)/xi*100. Selectivity of a product is calculated by the ratio between the amount of moles recovered of this product and the total amount of moles of products of reaction.

Examples 1 to 6

Not According to the Invention 0.5 moles of 240db or 1,1,1,2,3-pentachloropropane, 200 ml of anhydrous HF and 0.2 moles of catalyst are introduced in the autoclave. HF is then added continuously with a constant flow of 1 mol/h during 5 hours. Temperature is around 110° C. and absolute pressure is 9 bar. Different catalysts were investigated: SnCl4, SnCl4 doped with 0.03 moles of CsCl, TaCl5, TiCl4, SbCl5, liquid ionic ethylmethylimidazolium combined with SbCl5 catalyst.

For example 1, the sample of 240db used contained 10.7% of 240aa isomer (1,1,2,2,3-pentachloropropane). Conversion is given for each compound.

|  | Catalyst | Conversion % | Selectivities (%) | | | | | |
|---|---|---|---|---|---|---|---|---|
|  |  |  | 241 | 242 | 243db | 1230xa | 1233xf | Xi |
| Ex. 1 | SnCl4 | 240db: 76% 240aa: 15% | 86.6 | 5.8 | 0 | 1.9 | 0 | 5.7 |
| Ex. 2 | SnCl4 + CsCl | 44% | 77.4 | 8.9 | 0.2 | 2.2 | 6.5 | 3.8 |
| Ex. 3 | TaCl5 | 28% | 88.4 | 0.2 | 0 | 0.4 | 0 | 11.0 |

From example 4 to example 6, the organic phase has not been analyzed since it was something viscous. Only the analysis of the light fraction that could be collected is given.

|  | Catalyst |  |
|---|---|---|
| Ex. 4 | TiCl4 | 3.2 g collected molar comp: 54% 241, 1.5% 242, 32.8% 240db, 0% 1233xf |
| Ex. 5 | EmimCl + SbCl5 | 25 g collected molar comp: 4.1% 241, 50% 242, 26.4% 243db, 0.7% 1233xf, 5.2% 240db |
| Ex. 6 | SbCl5 | 32.8 g collected molar comp: 4.4% 241, 34.2% 242, 29.8% 243db, 0.5% 1233xf, 1.5% 240db |

Thus, when the medium is an HF medium, substantially no conversion into 1233xf takes place.

Examples 7 and 8

The same apparatus as examples 1 to 6 is used. 0.5 moles of 240db or 1,1,1,2,3-pentachloropropane and 0.2 moles of catalyst (0.2 moles of ethylmethylimidazolium chloride associated with 0.4 mole with SbCl$_5$, providing 0.2 moles of fluorinated complex catalyst emim$^+$Sb$_2$F$_{11}^-$emimcl) are introduced in the autoclave. In one case, 151 g of F122 or 1,1,2-trichloro-2,2-dichloroethane is added in the autoclave as solvent. HF is then added continuously with a constant flow of 1 mol/h during 5 hours. Temperature is 133° C. and absolute pressure is 9 bar. The set-point of the regulation of the condenser is always put at 90° C. In both cases, HCl was flowing through the autoclave to improve mixing and helping stripping out the products. The molar ratio HCl to 240db is near 2:1.

|  | Example 7 | Example 8 |
|---|---|---|
| F122 | — | 151 g |
| Conversion | 99.1% | 99.7% |
| Selectivity 1233xf (%) | 19.4 | 54.2 |
| Selectivity 242 (%) | 27.5 | 15.5 |
| Selectivity C6F6H2Cl2* (%) | 2.9 | 4.2 |
| others (%) | 43.6 | 18.1 |
| Total mass balance | 91.9 wt % | 91 wt % |

*C6F6H2Cl2 structure identified by NMR as CF3—CCl=CH—CH=CCl—CF3

Hence, 1233xf can be produced in substantial amounts. This is obtained in a medium which is not an acidic medium but rather an organic medium.

Examples 9 and 10

The same apparatus as the examples above is used. 0.5 moles of raw material sample (240db or 240db with 10% of 240aa), 0.2 moles of catalyst (0.2 moles of ethylmethylimidazolium chloride associated with 0.4 mole with SbCl$_5$, or also represented as 0.2 moles of fluorinated complex catalyst emim$^+$Sb$_2$F$_{11}^-$emimcl) and 2 moles of F122 are introduced in the autoclave. HF is then added continuously with a constant flow of 1 mol/h during 5 hours. Temperature is 135° C. and absolute pressure is 9 bar. The set-point of the regulation of the condenser is always put at 90° C. For both cases, Helium was flowing through the autoclave to improve mixing and helping to carry out the products. The flow of helium is 5 l/h.

|  | Example 10 | Example 11 |
|---|---|---|
| Raw material | 240db with 10% 240aa | Pure 240db |
| Conversion | 97.6% | 99.8% |
| 143a (%) | 0.03 | 0.03 |
| 1233xf (%) | 38.7 | 43.7 |
| 1223xd (%) | 1.2 | 1.65 |
| 1232xf (%) | 0.25 | 0.22 |
| 243db (%) | 1.37 | 1.26 |
| 233ab (%) | 0.65 | 3.95 |
| C6F6H2Cl2* (%) | 2.81 | 2.77 |
| 242 (%) | 34.5 | 29.6 |
| C6H4F4Cl4 (%) | 3.14 | 2.79 |
| others (%) | 15.43 | 14.1 |
| Total mass balance | 91 wt % | 93 wt % |

Thus, preparation of 1233xf can take place either from pure 240db or from 240db containing 240aa isomer. Without wishing to be bound, Applicant believes that the presence of the intermediate 242 is an indication that the reaction will proceed, although at a slower rate, from 240aa in a manner similar when compared to 240db.

Examples 11 and 12

In these examples, the reactants are introduced continuously through liquid massflowmeter. Between 100 and 200 ml of F122 or 1,1,2-trichloro-2,2-difluoroethane and 0.2 moles of catalyst (0.2 moles of ethylmethylimidazolium chloride associated with 0.4 mole with $SbCl_5$, providing 0.2 moles of fluorinated complex catalyst $emim^+Sb_2F_{11}^-$) are introduced in the autoclave as starting medium. HF and 240db are then added continuously in order that the molar ratio between HF and organic reactant is near 8. Temperature is 130-135° C. and absolute pressure is 8 bar. The set-point of the regulation of the condenser is put at 90° C. In example 11, no stabilizer is added to the organic reactant and in example 12 100 ppm of p-methoxyphenol are added to 240db compound. The impact of a stabilizer is thus investigated. In both cases, HCl was flowing through the autoclave (about 0.1 mol/h) to improve mixing and helping stripping out the products. The molar ratio HCl to 240db is near 2:1. The evolution of the molar composition of the outlet gas with time is followed by GC analysis. The results show the benefits associated with the use of the stabilizer, as can be deduced from the amount of C6 compound, notably.

Example 11

| Time | Molar composition of outlet gas (%) | | | | | | |
|---|---|---|---|---|---|---|---|
| H | 122 | 1112a | 244bb | 1233xf | 242 | 243db | C6F6H2Cl2 |
| 5 | 65.3 | 9.6 | 4.5 | 18.0 | 0.004 | 0.9 | 0.006 |
| 10.2 | 51.9 | 7.3 | 4.6 | 31.9 | 0 | 3.1 | 0.007 |
| 14.9 | 45.6 | 9.8 | 4.6 | 38.9 | 0.008 | 0 | 0 |
| 19.7 | 41.9 | 4.3 | 3.1 | 39.4 | 0.02 | 10.2 | 0.001 |
| 24.7 | 29.3 | 3.1 | 2.7 | 43.1 | 0.2 | 19.5 | 0.04 |
| 29.9 | 6.7 | 0.9 | 3.2 | 57.7 | 7.3 | 14.8 | 2.7 |
| 34.6 | 1.6 | 0.2 | 2.6 | 66.4 | 8.5 | 10.1 | 3.3 |
| 39.5 | 0.6 | 0.1 | 3.9 | 57.9 | 12.5 | 10.5 | 5.2 |
| 44.8 | 0.2 | 0.03 | 3.1 | 61.0 | 13.4 | 8.0 | 5.1 |
| 49.3 | 0.1 | 0 | 1.9 | 65.6 | 11.4 | 6.8 | 4.9 |
| 53.7 | 0.2 | 0.03 | 2.1 | 61.8 | 14.9 | 5.7 | 5.4 |
| 58.5 | 0.1 | 0.01 | 1.6 | 63.6 | 14.5 | 5.6 | 4.9 |
| 63.0 | 0.04 | 0.01 | 1.2 | 60.2 | 18.8 | 3.7 | 5.5 |
| 68.0 | 0.02 | 0.005 | 1.2 | 60.6 | 18.8 | 3.2 | 5.3 |
| 73.0 | 0 | 0 | 1.5 | 51.7 | 23.7 | 3.9 | 6.0 |
| 78.8 | 0 | 0 | 1.7 | 40.6 | 29.8 | 6.4 | 6.6 |
| 84.6 | 0.096 | 0.02 | 2.1 | 46.6 | 25.1 | 6.9 | 5.4 |
| 91.3 | 0.145 | 0.02 | 1.6 | 52.6 | 19.5 | 5.5 | 4.6 |
| 96.9 | 0 | 0.02 | 2.8 | 21.8 | 28.9 | 20.2 | 6.8 |
| 102.6 | 0 | 0.01 | 3.8 | 33.6 | 24.3 | 16.8 | 5.7 |
| 125.3 | 0 | 0.03 | 3.3 | 20.9 | 26.9 | 25.3 | 6.1 |
| 130.6 | 0 | 0.03 | 4.2 | 19.7 | 15.9 | 43.8 | 3.8 |

Example 12

| Time | Molar composition of outlet gas (%) | | | | | | |
|---|---|---|---|---|---|---|---|
| H | 122 | 1112a | 244bb | 1233xf | 242 | 243db | C6F6H2Cl2 |
| 5 | 54.5 | 7.6 | 0.4 | 36.0 | 0.06 | 0.05 | 0.02 |
| 10.2 | 52.4 | 8.5 | 1.0 | 36.8 | 0.02 | 0.3 | 0 |
| 15.8 | 50.8 | 6.2 | 0.6 | 40.4 | 0.03 | 1.0 | 0.007 |
| 22.4 | 33.4 | 3.7 | 0.4 | 50.6 | 4.6 | 2.4 | 0.9 |
| 38.6 | 2.2 | 0.2 | 0.2 | 75.7 | 11.2 | 0.6 | 1.8 |
| 45.6 | 1.6 | 0.2 | 0.7 | 72.3 | 14.8 | 0.5 | 2.2 |
| 62.5 | 0.8 | 0.1 | 1.0 | 67.0 | 18.5 | 2.3 | 1.8 |
| 68.7 | 1.7 | 0.2 | 1.0 | 18.2 | 47.5 | 9.2 | 4.7 |
| 85.6 | 0.3 | 0.05 | 2.1 | 60.4 | 20.2 | 7.1 | 1.6 |
| 91.5 | 0.2 | 0.05 | 2.0 | 59.4 | 21.8 | 6.2 | 1.6 |
| 97 | 0.1 | 0.04 | 2.3 | 60.8 | 20.3 | 6.9 | 1.5 |
| 113.4 | 0.04 | 0.02 | 1.2 | 66.3 | 20.1 | 3.0 | 1.6 |
| 120.1 | 0.04 | 0.01 | 1.1 | 64.0 | 21.9 | 2.7 | 1.9 |
| 138.9 | 0 | 0 | 1.0 | 67.5 | 20.5 | 2.0 | 1.9 |

Example 13

100 ml of F122 or 1,1,2-trichloro-2,2-difluoroethane and 0.2 moles of catalyst (0.2 moles of ethylmethylimidazolium chloride associated with 0.4 mole with $SbCl_5$, providing 0.2 moles of fluorinated complex catalyst $emim^+Sb_2F_{11}^-$) are introduced in the autoclave as starting medium. HF and 240db are then added continuously in order that the molar ratio between HF and organic reactant is near 8. 240db solution has been first diluted with 122 (400 g of 122 per kg of 240db) so that both components are cofed into the reactor. 122 is cofed in order to compensate the stripping of the solvent during the continuous run. Temperature is 130-135° C. and absolute pressure is 8 bar. The set-point of the regulation of the condenser is put at 90° C. HCl flows through the autoclave (around 0.1 mol/h) to improve mixing and helping stripping out the products. The molar ratio HCl to 240db is near 2:1. The evolution of the molar composition of the outlet gas with time is followed by GC analysis.

Example 13

| Time | Molar composition of outlet gas (%) | | | | | | |
|---|---|---|---|---|---|---|---|
| h | 122 | 1112a | 244bb | 1233xf | 242 | 243db | C6F6H2Cl2 |
| 6.5 | 52.4 | 2.5 | 0.9 | 42.0 | 0.39 | 0.1 | 0.03 |
| 29.5 | 55.9 | 2.8 | 1.1 | 36.8 | 0.28 | 1.2 | 0.03 |
| 46.7 | 41.7 | 2.2 | 0.5 | 46.3 | 4.2 | 0.9 | 0.7 |
| 53.4 | 36.2 | 2.2 | 0.5 | 47.3 | 7.6 | 0.7 | 1.6 |
| 69.9 | 33.3 | 1.3 | 0.6 | 49.0 | 9.9 | 0.9 | 2.0 |
| 76.5 | 31.85 | 1.4 | 0.7 | 46.1 | 12.9 | 1.4 | 2.5 |
| 93.8 | 30.3 | 1.3 | 1.2 | 40.3 | 16.6 | 3.9 | 2.9 |
| 99.8 | 30.72 | 1.3 | 1.6 | 40.2 | 15.3 | 4.9 | 2.7 |
| 122.4 | 40.1 | 1.8 | 1.7 | 35.2 | 10.9 | 6.0 | 1.4 |
| 127.9 | 36.6 | 1.9 | 1.2 | 38.6 | 10.6 | 6.3 | 1.6 |
| 145.4 | 27.3 | 1.4 | 0.7 | 51.6 | 11.5 | 2.1 | 1.8 |
| 151.9 | 27.3 | 1.5 | 0.7 | 48.9 | 13.4 | 1.9 | 2.1 |
| 168.9 | 27.0 | 1.4 | 0.7 | 50.5 | 12.6 | 1.5 | 2.1 |
| 175.4 | 27.6 | 1.5 | 0.7 | 50.2 | 12.2 | 1.5 | 1.9 |
| 192.8 | 27.1 | 1.3 | 0.8 | 50.2 | 12.9 | 1.5 | 2.2 |
| 199.1 | 27.9 | 1.3 | 0.9 | 52.4 | 10.3 | 1.6 | 1.6 |
| 216.0 | 27.4 | 1.3 | 0.9 | 50.4 | 12.1 | 1.6 | 2.1 |

The invention claimed is:

1. A process for preparing 2-chloro-3,3,3-trifluoropropene comprising fluorinating in a liquid phase in an organic medium a reactant comprising 1,1,1,2,3-pentachloropropane or/and 1,1,2,2,3-pentachloropropane in the presence of a catalyst, wherein the organic medium is selected from the group consisting of 1,2-dichloroethane, 1,2,3-trichloropropane, 1-chloro-1-fluoroethane, 1,1-difluoroethane, 1,1-dichloro ethane and 1,3-dichloro-1-fluorobutane, tetrachlorofluoropropane isomers, trichlorodifluoropropane isomers and dichlorotrifluoropropane isomers, 1,1,1,3,3-pentafluorobutane and 1,1,2-trichloro-2,2-difluoroethane, nitrated solvents including nitromethane and nitrobenzene, sulfones including tetramethylene sulfone and dimethyl sulfone, 1,1,2-trichloro-2-fluoroethane, perchloroethylene, and mixtures thereof.

2. The process according to claim 1, in which the solvent is present in a quantity to provide a dilution ratio of at least 20%.

3. The process according to claim 1, in which the catalyst is an ionic liquid.

4. The process according to claim 1, in which the molar ratio catalyst to reactant lies between 2 mol % and 90 mol %.

5. The process according to claim 1 further comprising adding chlorine during the reaction, in a molar ratio from 0.05 to 20 mole % of chlorine per mole of reactant.

6. The process according to claim 1, further comprising injecting a gas.

7. The process according to the claim 6, in which the ratio of the flow of gas, compared to the flow of reactant is between about 0.5:1 and 5:1.

8. The process according to claim 1, in which the 2-chloro-3,3,3-trifluoropropene is withdrawn in the gaseous state.

9. The process according to claim 1, in which the reactant comprises up to 20 mol % of 1,1,2,2,3-pentachloropropane.

10. The process according to claim 9, in which the temperature of the reaction ranges between 30° C. and 200° C.

11. The process according to claim 1, in which the pressure of the reaction is higher than 2 bar.

12. The process according to claim 1, in which the molar ratio of HF to reactants is between 0.5:1 and 50:1.

13. The process according to claim 1, further comprising adding a stabilizer, selected from the group consisting of p-methoxyphenol, t-amylphenol, thymol, limonene, d,l-limonene, quinones, hydroquinones, epoxides, amines and their mixtures.

14. The process according to claim 13, where the stabilizer is used in an amount of 5-1000 ppm.

15. The process according to claim 1, comprising: (i) contacting 1,1,1,2,3-pentachloropropane or/and 1,1,2,2,3-pentachloropropane with hydrogen fluoride in a liquid phase in an organic medium under conditions sufficient to form a reaction mixture comprising 2-chloro-3,3,3-trifluoropropene; (ii) separating the reaction mixture into a first stream comprising HCl, and a second stream comprising HF and 2-chloro-3,3,3-trifluoropropene.

16. The process according to claim 15, wherein the second stream comprises between 30 mol % and 70 mol % of 1233xf, between 30 mol % and 70 mol % of HF and less than 10 mol %, of compounds of the series 242 and 243.

17. The process according to claim 15, wherein said separating is a distillation.

18. The process according to claim 15, further comprising separating said second stream into a HF stream containing mainly HF, and an organic stream containing 2-chloro-3,3,3-trifluoropropene.

19. The process according to claim 18, further comprising purifying the organic stream.

20. The process according to claim 1, further comprising purging heavies from said reaction mixture.

* * * * *